United States Patent
Orser et al.

(10) Patent No.: US 7,160,690 B2
(45) Date of Patent: Jan. 9, 2007

(54) NITRATE SENSOR

(75) Inventors: Cindy Orser, McLean, VA (US); Denis Pilloud, La Croix-de-Rozon (CH)

(73) Assignee: Arete Associates, Sherman Oaks, CA (US)

( * ) Notice: Subject to any disclaimer, the term of this patent is extended or adjusted under 35 U.S.C. 154(b) by 328 days.

(21) Appl. No.: 10/290,108

(22) Filed: Nov. 6, 2002

(65) Prior Publication Data

US 2003/0232322 A1 Dec. 18, 2003

Related U.S. Application Data

(60) Provisional application No. 60/337,741, filed on Nov. 6, 2001.

(51) Int. Cl.
*G01N 33/53* (2006.01)
*G01N 33/00* (2006.01)
*C12Q 1/00* (2006.01)
*C12Q 1/26* (2006.01)
*C12N 9/06* (2006.01)

(52) U.S. Cl. ............... 435/7.7; 435/4; 435/25; 435/189; 435/191; 436/110

(58) Field of Classification Search ............ 435/4, 435/24, 7.7, 189, 191, 25, 185; 436/110
See application file for complete search history.

(56) References Cited

OTHER PUBLICATIONS

Kiang et al. "Enzymatic Determination of Nitrate: Fluorometric Detection after Reduction with Nitrate Reductase" Anal. Chem. (1978) 50(9): 1323-1325.*
Campbell, W. "Nitrate Reductase Structure, Function and Regulation: Bridging the Gap between Biochemistry and Physiology" Ann. Rev. Plant Physiol. Plant Mol. Biol. (1999) 50: 277-303.*

* cited by examiner

*Primary Examiner*—Jean C. Witz
*Assistant Examiner*—Susan Hanley
(74) *Attorney, Agent, or Firm*—Peter I. Lippman

(57) ABSTRACT

A biosensor method and apparatus for detecting and measuring nitrate. The biosensor is based on the fluorescence properties of a receptor molecule fragment. The biosensor apparatus contains the active-site fragment of the receptor molecule for detecting nitrate. Both the biosensor method and apparatus provide reversible and sensitive detection of nitrate in the form of a versatile method and device.

21 Claims, 13 Drawing Sheets

Figure 2
a 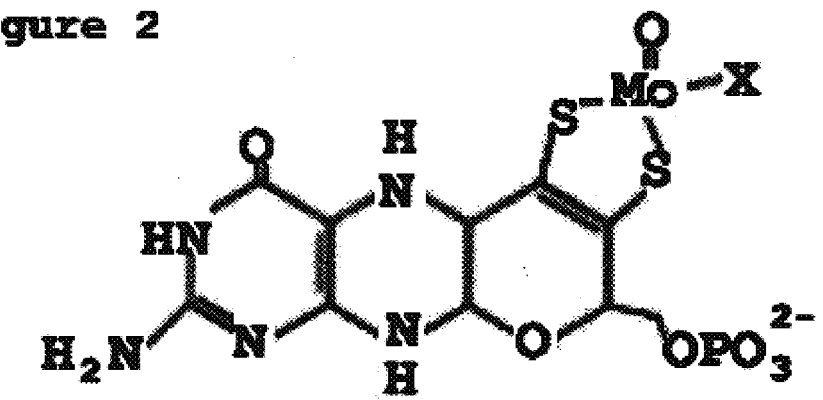
b 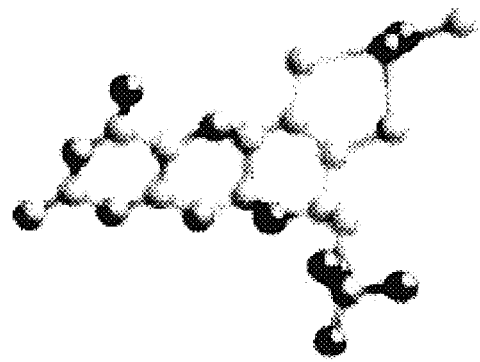
c 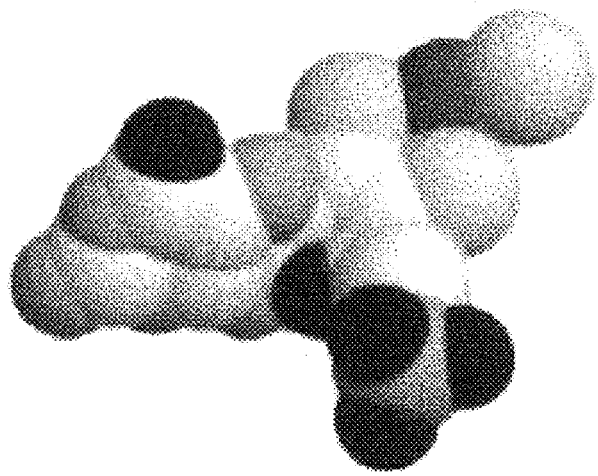

NITRATE SENSOR

This document claims priority of U.S. provisional patent applications, Ser. No. 60/337,741 filed on Nov. 6, 2001. This document hereby incorporates by reference in to this application provisional application Ser. No. 60/293,865 filed on May 25, 2001 by Denis Pilloud, and references wholly incorporated therein, namely, 1) technical papers cited at pages 4, 6, 7, 8, 17, 18 and 19 thereof; 2) application Ser. No. 10/155,745, filed May 31, 2002; and provisional application Ser. No. 60/295,456 filed on May 31, 2001, by Cindy Orser, et al.

BACKGROUND

1. Field of the Invention

This invention relates generally to biosensors; and more particularly to a biosensor method for detecting nitrate based on the fluorescence properties of a receptor molecule and a biosensor apparatus containing the active-site fragment of the receptor molecule for detecting nitrate.

2. Related Art

Nitrate ion from fertilizers and treated sewage has reached disquietingly high concentrations in water supplies all around the world. In the United States, the Environmental Protection Agency (EPA) has fixed an allowable upper limit of 10 ppm for $NO_3^-$ nitrogen ($NO_3$—N) in drinking water. This is to prevent illnesses caused by higher nitrate levels such as methemoglobinemia ("blue baby syndrome") in bottle-fed infants. The health and environmental risks associated with elevated nitrate levels are the following:

Methemoglobinemia. Elevated nitrate levels poses a risk to infants and can lead to methemoglobinemia, or "blue baby syndrome". Elevated levels of nitrate lead to a build-up of nitrite in the gastrointestinal tract by nitrate reducing bacteria. The excess nitrite moves into the bloodstream where it binds strongly to blood hemoglobin and impairs the delivery of oxygen to the baby.

A recent study from the University of Iowa has shown a link between nitrate levels in drinking water and bladder cancer in women (Weyer, et al., 2001)

Blood and serum nitrate levels can become elevated as the result of increased production of nitric oxide (NO). Nitric oxide is an unstable gaseous compound that readily diffuses into body fluids where it can be converted to nitrate, nitrite or S-nitrothiol. NO levels rise during heightened immune-response such as occurs during sepsis, organ failure or graft-rejection.

There is also a concern over excess nitrates and aquatic biology. When a nitrogen limited eco-system is supplied with high levels of nitrate, significant increases in the levels of phytoplankton (algae) and macrophytes (aquatic plants) can occur. This poses a significant threat to these fragile ecosystems. The recommended levels of nitrates to avoid the propagation of algal blooms is between 0.1 to 1 mg/l (NOAA/EPA).

As the major environmental release of nitrate arises from its use in fertilizers, it is unlikely that the nitrate problem will disappear anytime soon. Thus, there will be a continued need to monitor nitrates in finished drinking water, watersheds, industrial wastewater, private wells and estuaries. Additionally, nitrate contamination of source water will always be a concern for industries that depend on water purity for the manufacturing of their finished product. The data related to nitrate as a contaminant demonstrates the scope of the problem:

According to the Toxic Release Inventory database nearly 60 million pounds of nitrate were released into water between 1987 and 1993. An additional 53 million pounds of nitrate was released into land over this same period. Nitrate is highly soluble and only weakly retained by soils, such that a large portion of the nitrate released to the ground will eventually end up in the water.

According to the EPA there were 14,000 measurement/recording violations for nitrate in the fiscal year 2000. These involved over 11,000 systems and affected over 4 million citizens. Similar numbers were recorded for the years between 1997 and 1999.

According to the EPA statistics regarding nitrate violations, for the fiscal year 2000, there were 804 violations occurring in 457 sites affecting a population of approximately 460,000 people with nitrate levels that exceeded the maximum contaminant level (MCL).

The number stated above for nitrate violations does not reflect the additional potential for exposure to elevated nitrate levels in the more than 15 million private wells in the United States. A 1992 survey conducted by the Office of Pesticides and Toxic substances of the EPA, estimated that 22,000 infants less than one year of age had well-water that exceeded the 10 ppm standard.

It is therefore imperative to develop a reliable, sensitive and selective device to monitor drinking water for nitrate ions. There are a number of commercially available kits for measuring nitrate. These kits utilize a variety of sensing technologies. The EPA Office of Ground Water and Drinking Water maintains a database of approved analytical methods for drinking water compliance monitoring. The methods currently approved for monitoring nitrates are cadmium reduction, ion chromatography and ion-specific electrodes. It is our belief that none of these approaches provides a measurement technology that is rugged, sensitive and suited to the broad spectrum of water sources that need to be monitored. The most sensitive devices, such as ion chromatography, are not portable or adaptable for field-testing without shipping the samples. While many of the field test kits are portable they introduce the opportunity for operator error, in terms of mixing the reagents and interpreting the results. A survey of current nitrate detection technologies is presented in FIG. 22.

The Safe Drinking Water Act (SDWA) is the main federal law that ensures the quality of Americans' drinking water. Under the SDWA the United States Environmental Protection Agency (USEPA) has established guidelines and standards for drinking water quality. In 1996, Congress amended the SDWA to emphasize the importance of sound scientific assessment of the health risks related to water pollutants and contaminants. Our drinking water has shown remarkable improvements since the SDWA was adopted, however, there are growing concerns about the future of safe drinking water and water resources in the United States.

The cost associated with ensuring the safety of our drinking water is growing and will require a considerable input to upgrade the deteriorating water infrastructure in the United States.

Rural and tribal populations in the United States that do not have water that meets current standards. The prospect of increasing cost is an even greater concern to the rural water community, where economics of maintaining a safe water supply are the greatest challenge.

The standards may not be sufficient to ensure the safety of certain vulnerable sub-populations such as the elderly, infants, pregnant women and the immuno-compromised. A University of Iowa study has shown that the incidence of bladder cancer was nearly 3 fold higher for the group of women whose water supply had an average nitrate level of 2.46 mg/L nitrate-nitrogen versus those whose water supply contained an average of 0.36 mg/L nitrate-nitrogen. Alarmingly, this level is below the standard indicated under the SWDA.

There is a heightened concern about the health risks associated with exposure to contaminants such as arsenic, nitrate, heavy metals, disinfection by-products and other agents via drinking water. There is the prospect that even in the face of increasing operational cost to produce safe water that we may need to regulate and monitor even more contaminants.

Effective monitoring is a critical component for providing clean, safe drinking water and protecting our water resources. The technology associated with water monitoring must be upgraded to meet the needs of the water and wastewater industries.

There is a need to increase our overall monitoring capabilities to accurately assess the effectiveness of government sponsored water resource management programs.

To develop cost-effective monitoring and processing technologies that will allow the rural and tribal communities to attain a high standard for their drinking water without taxing their limited economic resources.

To produce devices that emphasize simplicity and multi-contaminant analytical capabilities that will enable the individual operator to work more efficiently. This will eliminate the need for third party testing and concerns over shipping and custody of samples.

Design devices for in-line monitoring with direct data read-out to provide operators with critical information in real-time. This is essential for prompt decision making during critical events such as spills and floods.

The quantitative assessment of single common or trace amounts of nitrate in solution depends primarily on chemical and/or analytical separation and detection technologies. These methodologies often require sample preparation, the use of various reagents and some physical transducer of the final product of the chemistry to provide quantitative information. Examples of physical transducers include optical detection, electrochemical, and a broad number of physical detection modes. See Riedel, K., 1998, in Ramsay, G. [ed.] *Commercial Biosensors*, Vol. 148, Chemical Analysis, John Wiley & Sons, New York, pp. 267–294; Kress-Rogers, E. 1997, *Handbook of Biosensors and Electronic Noses: Medicine, Food, and the Environment,* [ed., Kress-Rogers, E.], CRC Press, Boca Raton. In general, these technologies are time consuming, costly and require skilled operators but can provide sensitive and reliable quantification of specific analytes. Analytical methods that are rapid and perhaps less costly, may not be as sensitive or reliable as transducer methods, but may still meet the detection and/or quantification requirements.

More recently, sensors based upon biological sensing elements have been developed and exploited for detecting and quantifying a broad range of analytes from ions, metals, and small organics to proteins, lipids, nucleic acids and even whole organisms. These elements include enzymes, antibodies, RNA/DNA probes, membrane channels, whole cells, organs and even whole multicellular organisms. These types of sensors are called biosensors in that the sensing element is of biological origin.

Biosensors are monitoring devices composed of two elements, the first of which is the signal capture component that uses a biological entity such as an enzyme, antibody or cell surface receptor. The second part is the signal transduction element that converts the biological response into a measurable signal like fluorescence, electric current or potential. Biosensors have been described for the determination of more than thirty different environmentally relevant compounds (Riedel, 1998).

Biosensors can achieve the same or greater selectivity and sensitivity as analytical methods, and many allow detection and/or quantification in the absence of reagents and sample preparation, and most often do not require a skilled operator. Because the sensing element in a biosensor is typically very small and because detection is based upon molecular recognition of individual ligand molecules, biosensor devices can be very small and portable, thereby greatly expanding the utility and application of sensing and monitoring technologies.

Biosensors for a broad range of analytes including environmental contaminants and analytes relevant to industrial processes, medical diagnostics and law enforcement have been reported in the scientific and patent literature, though only a few technologies have obtained commercial success to date. See Riedel, K., 1998, in Ramsay, G. [ed.] *Commercial Biosensors*, Vol. 148, Chemical Analysis, John Wiley & Sons, New York, pp. 267–294; Kress-Rogers, E. 1997, *Handbook of Biosensors and Electronic Noses: Medicine, Food, and the Environment,* [ed., Kress-Rogers, E.], CRC Press, Boca Raton; Scheller, F. W. and Pfeiffer, D. 1997, in id; Urban, G. 1997 in id.

Enzyme-based biosensors that exploit oxidoreductases have been described. Nitrate reductase (NR), an oxidoreductase, from a variety of sources (bacteria, fungi, and vascular plants) has been used to assay nitrate in environmental or medical samples, in biosensor applications and in bioremediation applications. Nitrate reductases (NR) from different eukaryotic genera (yeast, algae, vascular plants) all share a common subunit structure and a catalytic function—the reduction of nitrate ($NO_3-$) to nitrite ($NO_2-$). A number of amperometric sensors exploiting various nitrate reductases have been described. As in any amperometric sensor, the Faradic current derived from the redox reaction at the electrode is measured. Glazier, S. A., Campbell, E. R. and Campbell, W. H. (1998, Anal. Chem. 70:1511–1515) generated an NR-based nitrate sensor that exploits a vascular plant (corn) NR and glassy carbon electrodes for the measurement of nitrate in buffered solutions.

Amperometric biosensors have been developed to take advantage of the redox properties of enzymes. In some applications, the enzymes may be maintained in solution on the surface of the electrode by using a semi permeable membrane, or they may be immobilized onto the surface of the electrode either covalently through some cross-linking chemistry or entrapped in a cross-linked matrix which adheres to the surface of the electrode. In the latter case, the matrix may be a protein or sol-gel, while in other it may be a conducting polymer that can serve to provide and enhance the electrical continuum between the redox centers of the enzyme and the electrode.

Moretto et al. (1998, Anal. Chem. 70:2163–2166; Ramsay, G. and Wolpert, S. M. 1997, *Polymeric Mat. Sci. Engineer.* 76:612–613) used an ultrathin film composite membrane technology to generate a nitrate biosensor. An ultra thin film of 1-methyl-3-(pyrrol-1-methyl) pyridinium tetrafluorborate was polymerized on an alumina support membrane, which has been coated with a film of gold. This film blocked the loss of methyl viologen, the electron donor to NR, and the free solution of *Aspergillis* sp. NR while allowing anions (e.g., nitrate) to flow freely to the enzyme. The enzyme activity was coupled to a glassy carbon electrode for amperometric assessment of nitrate levels in buffered solutions and in buffered natural water samples. In all cases where NR was "wired" with alkylpyrroleviologen-based redox polymers, enzyme activity was low. More recently, it has been demonstrated that such redox polymers and even the monomers in solution strongly (>90% loss of activity) inactivate NR (Ramsay and Wolpert, 1999, Anal. Chem. 71:504–506

Essentially all enzyme-based NR biosensors described to date lack stability, ruggedness or real-world applicability. In general, they show very limited periods of operational activity, from a few hours to a couple of days even under laboratory conditions. Lack of long-term stability and functionality typically has been ascribed to enzyme instability, loss of required enzyme mediators or both. Though numerous attempts have been made to overcome these features that limit their practical utilization and commercialization, we believe the present invention overcomes the bulk of the shortcomings of the existing technologies.

Enzyme-based amperometric sensors generally suffer from several major limitations: 1) traditional methods of electrode preparation with each of the three electrode cells comprised of different materials make modeled performances difficult to derive, 2) insufficient enzyme availability/high cost of enzyme preparation, 3) instability of enzyme and/or mediators under ambient conditions, 4) inadequate transducers for reporting enzyme activity, 5) inefficient enzyme immobilization or coupling to electrode, 6) end-product inhibition, and 7) enzyme specificity lacking, 8) a high cost of production and/or multiple steps in preparation.

As can now be seen, the related art remains subject to significant problems, and the efforts outlined above—although praiseworthy—have left room for considerable refinement.

SUMMARY OF THE DISCLOSURE

The present invention introduces such refinement. The invention has at least two independently usable facets or aspects, which will now be introduced.

These aspects or facets, however, do have several elements in common. The common parts will be described first.

In its preferred embodiments, the present invention is a biosensor method for detecting nitrate in a test specimen. The method includes exposing a fluorescence emitting molecule to a test sample and then measuring any resulting decrease in fluorescence.

Now in preferred embodiments of a first of the independent aspects or facets of the invention, the quantity of nitrate in a test sample can be calculated. The nitrate quantity is proportional to the measured decrease in fluorescence. In other words, the nitrate quenches the fluorescence signal. The fluorescence signal comes from a fluorescence emitter which in preferred embodiments of the invention is a component of nitrate reductase. The component can be part of a domain region of nitrate reductase—specically, the Molybdenum-Molybdopterin (Mo-MPT)center.

In a preferred embodiment, the Mo-MPT can be obtained by cleaving the Mo-MPT domain of nitrate reductase and filtering the cleavage products to isolate the Mo-MPT.

In another preferred embodiment, the Mo-MPT can be obtained by gene subcloning the fragment. This can be done by inserting a cloned Mo-MPT fragment into bacterial expression vectors, identifying vectors which screen positive for the insertion and then isolating the Mo-MPT clone from the those vectors which screened positive.

The gene subcloning step can be preceded by an amplification step where the Mo-MPT fragment is cleaved from nitrate reductase and is then amplified using polymerase chain reaction and subcloning.

In particularly preferred embodiments, the measuring step of the method has a nitrate detection sensitivity of one part per billion. In other preferred embodiments, the measuring step of the method has a nitrate detection sensitivity of ten parts per million. Yet, in other preferred embodiments, the measuring step of the method has a nitrate detection sensitivity of one hundred parts per million.

The biosensor method is very versatile and in particularly preferred embodiments allows immersing the emitter in the test specimen. In other embodiments, the emitter is disposed on a structural support. The structural support may comprise a wall of a chamber, room or passageway. In other particularly preferred embodiments, the structural support may be any one of a gel matrix, a microsolution, an electrode, a microchip, a fiber optic cable and a solid particle. Additionally, in preferred embodiments, the test specimen may be substantially continuously monitored.

Application of this method extends to any one of natural natural fresh, marine and estuarine waters, municipal and rural drinking water sources, aqueous solutions associated with wastewater treatment facilities, aqueous solutions associated with industrial process streams, pharmaceuticals, nutritional supplements, foodstuffs, beverages, body fluids, chemicals, water specimens, biologicals, vapors, and derivatives thereof.

The foregoing may be a description or definition of the first facet or aspect of the present invention in its broadest or most general terms. Even in such general or broad form, however, as can now be seen the first aspect of the invention resolves the previously outlined problems of the prior art.

In particular the method of the invention doesn't necessarily require the use of electrodes or preparation of several different enzyme coated electrode materials, unlike many enzyme-based amperometric sensors of the prior art. Also, there is little concern for insufficient availability of an enzyme, since the method of this invention is based on a fragment of an enzyme which can easily be amplified and cloned. Furthermore, the adaptability of this method allows the emitter to be immersed in a test sample or disposed on a variety of substrates, thus there is less concern regarding immobilization techniques or coupling to an electrode. Also, the method is based on commonly used and widely available instrumentation, and as a result it is economical and uncomplicated.

Now turning to a second of the independent facets or aspects of the invention: the invention is a biosensor apparatus for detecting nitrate in a test specimen. The apparatus includes an enclosure containing a fluorescence emitter and means for adding the specimen to the enclosure. A detector senses the fluorescence of the emitter and measures decrease in the fluorescence after addition of the sample.

In preferred embodiments of this second facet, the apparatus includes a processor for receiving information derived from the sensed fluorescence, and means that are responsive to the processor for communicating a corresponding concentration of nitrate in the specimen.

In another preferred embodiment, the apparatus includes a memory device which holding a calibration formula and a portion of the processor receives the derived information and applying it to the calibration formula for calculating the concentration for display.

In a particularly preferred embodiment, the apparatus also includes automatic means for monitoring the displayed concentration and utilization means that are responsive to the monitoring means. The utilization means can be selected from any one of an annunciator for alerting an operator to the communicated concentration; automatically controlled robotics; an automatically controlled nitrate injection system; and an automatically controlled lock or other automatic access-control device for enabling or not enabling access to a facility, an apparatus, credit, information, or a service.

Additionally, in preferred embodiments, the enclosure can be a sample cell. The enclosure can also be a room or passageway. In preferred embodiments, the enclosure includes a structure for supporting the emitter. It is particularly preferred that the structure can be selected from any of a gel matrix, a microsolution, an electrode, a microchip, a fiber optics cable, a waveguide or a solid particle.

In this way this second facet of the invention too adapts to a wide variety of applications and is based on commonly used and widely available instrumentation. Hence this facet of the invention promotes and enables the desired economy that accompanies use of a sensitive and easily adaptable biosensor apparatus.

All of the foregoing operational principles and advantages of the present invention will be more fully appreciated upon consideration of the following detailed description, with reference to the appended drawings.

BRIEF DESCRIPTION OF THE DRAWINGS

FIGS. 2a through c are structural diagrams of the Mo-MPT subunit of nitrate reductase, wherein (a) shows its chemical skeletal structure, (b) shows a ball-and-stick model of its structure and (c) shows a space-filling model of its structure, (See W. H. Campbell, *Annu. Rev. Plant Physiol. Plant Mol. Biol.* 1999, 50, 277–303.);

DETAILED DESCRIPTION OF THE PREFERRED EMBODIMENTS

Figure 1:
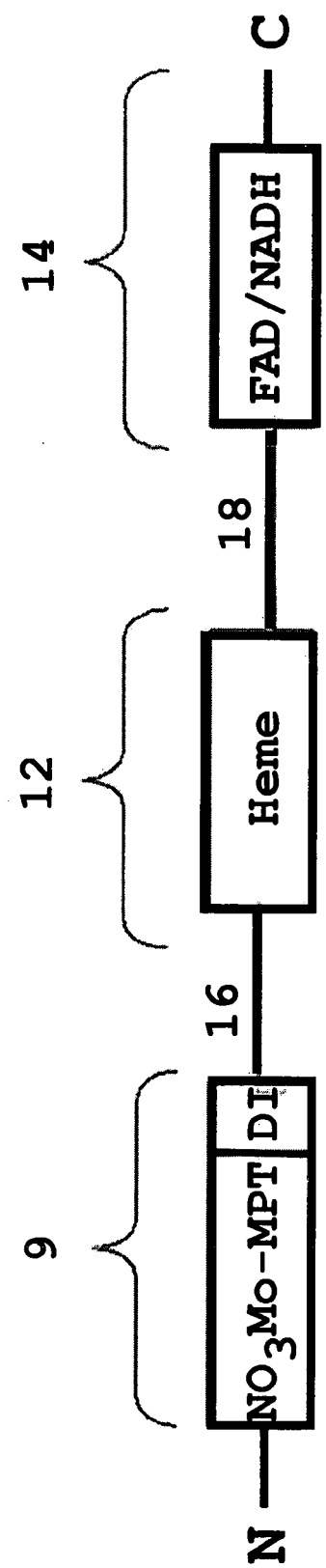
FIG. 1 is a schematic sequence model of nitrate reductase.

As used herein, the term "biosensor" refers to a sensing method for detecting nitrate which comprises binding of nitrate in a test specimen to a fluorescence-signal emitter of the invention. Biosensors use catalysis and affinity interactions, generally using agents derived from biological systems or recombinant biological systems. In the present invention, the biosensor uses agents that are derived from such biological systems. The term "biosensor" also refers to a self-contained analytical device that responds selectively and reversibly to the presence or concentration of nitrate in a test specimen. Accordingly, the device of the present invention comprises a biosensor for practical applications in medicine, chemical monitoring, environmental protection, and process stream monitoring in various industrial applications such as food or beverage processing.

As used herein, the term "test specimen" is used to refer to a candidate material that might or might not contain nitrate which the methods and device of the invention are detecting. In other words, nitrate, is the chemical entity the methods or device are looking for, and the test specimen is the material in which the methods or device are looking for it.

Another definition of the term "fluorescence-signal emitter" as used herein is a molecule capable of emitting a fluorescence signal. The fluorescence-signal emitter may be chemically synthesized or may occur in nature.

The practice of the present invention will employ, unless otherwise indicated, standard techniques, materials, and equipment in biosensors, and electronics for detecting, monitoring, and processing electrical characteristic changes of sensing elements. Factors, techniques, and equipment involved in biosensor construction, performance and application of biosensors to health care, control of industrial processes, environmental monitoring are explained fully in the literature. The electroanalytical methods of potentiometry, voltammetry and conductivity, chip and biosensor system device construction are disclosed and explained in standard references. Also available in the literature are methods for optimizing performance factors: selectivity, linear range, calibration, reproducibility, response time, life time and the factors affecting biosensor performance (See, e.g., Janata, J., *Principles of Chemical Sensors,* (1989), Plenum Press; Eggins, B. R., *Biosensors—An Introduction,* (1996), John Wiley & Sons Ltd.; Kress-Rogers, E., ed., *Handbook of Biosensors and Electronic Noses, Medicine, Food and the Environment* (1997), CRC Press; Fraser, D. M., *Biosensors in the Body: Continuous in Vivo Monitoring,* (1997), John Wiley & Sons; Bickerstaff, G. F. ed., (1997) *Immobilization of Enzymes and Cells.*

Biosensor Method

An essential element to the application of our approach is a basic understanding of the protein to be modeled. To demonstrate the feasibility of our approach we chose to model the active site chemistry for the enzyme nitrate reductase, as a means of developing a nitrate sensor. This implementation of the present invention is described in detail by incorporation of materials previously deposited in the Patent and Trademark Office on May 25, 2001 as a coowned provisional application entitled, *Nitrate Amperometric Sensor for Nitrate Detection Using a Synthetic Substrate,* by inventors Pilloud, McGowan, Farruggia, and Morris, provisional application No. 60/293,865 herein incorporated in its entirety by reference. It is also summarily described in this application as follows.

In nature, for the synthesis and utilization of proteins and nucleic acids, the sources of nitrogen are provided by two major pathways: nitrate assimilation and nitrogen fixation. Nitrate assimilation by higher plants, algae, fungi, yeasts and bacteria is significantly more important than nitrogen fixation. Nitrate assimilation is achieved by the enzyme nitrate reductase (NR), which reduces nitrate to nitrite ($NO_2^-$). Accordingly, the nitrate reductase enzyme catalyzes the following reaction:

$NO_3^-$+NADH à $NO_2^-$+$NAD^+$+$OH^-$

In the reaction nitrate is reduced to nitrite and nicotinamide adenine dinucleotide (NADH) is converted to its oxidized form, $NAD^+$. The reaction is essentially irreversible (DG=−34.2 kcal/mol) and is the rate-limiting step for the acquisition of nitrogen for most plants, algae and fungi (REF: Campbell, 1999). The nitrate reductase enzyme is a homodimer containing two identical subunits ranging from 100–145 kDaltons depending on the source organism. Each nitrate reductase monomer is composed of three distinct domains; the flavin adenine dinucleotide (FAD) 14, the heme 12 and molybdenum 9 domains as shown in FIG. 1. Electrons are transferred through a series of reactions beginning with the FAD region 14, passing through the heme center 12 and terminating in the molybdenum-containing region 9.

The active site for nitrate binding and reduction is located in the molybdenum-containing domain 9 as shown in FIG. 1. The other domains shown in FIG. 1 function primarily to donate the electrons that ultimately serve to reduce the nitrate. It has been shown that these other domains are not necessary for the reduction of nitrate to occur, provided that a secondary source of electrons, such as bromo-phenol blue or methyl viologen, is added (Kubo, et al., 1988; Solomonson and Barber, 1990; Mertens et al., 2000)

Although, the crystal structure of nitrate reductase remains unresolved, the active site described above was uncovered based on the known structures for several related molybdenum-containing enzymes (Boyington et al., 1997; Schindelin et al., 1996; Romao et al., 1995; Schneider et al., 1996). FIG. 2 shows the chemical and three-dimensional structures of the molybdenum-containing domain 10.

The bacterial nitrate reductases can be classified either as membrane-bound, cytoplasmic or periplasmic according to their cellular location. Sequence comparisons among these three classes reveal some distinctions in their amino acid sequences that are directly related to functional differences among the different nitrate reductase sub-classes (Blasco et al., 1990; Wootton et al., 1991; Berks et al., 1995; Trieber et al., 1996).

From this combination of structural modeling and sequence analysis a picture of the active-site chemistry for the nitrate reductase enzymes emerged. It has been reported that a cluster of cysteine residues located near the active site play an essential role in mediating electron transfer in the enzyme. Cysteine residues contain free sulfhydryl groups in their side chains that allows them to enter into thiol linkages. Their role in the reduction of nitrate comes from their ability to bind iron through forming iron-sulfur [Fe—S] pairs, where the iron is involved in the transfer of electrons (Garde et al, 1995). Magalon and co-workers, performed extensive analysis of the *E. Coli* nitrate reductase active site. This group was particularly interested in the role played by a specific histidine residue located at amino acid site 50 of the *E. Coli* nitrate reductase.

In other nitrate reductases, this residue is one of the cysteines (mentioned above) that is involved in binding iron. They discovered, however, that in the *E. Coli* enzyme, this residue is required to adjust the coordination state of the molybdenum during the reduction reaction cycle (Magalon et al., 1998). Using electron paramagnetic resonance (EPR) they showed that the molybdenum shuttled through coordinations of state 5 and 6 during the reaction. These results allowed us to reduce a complicated enzymatic reaction to its key active site components: a molybdenum metal that can shuttle between +5 and +6 coordinations, sulfhydryl containing amino acids to form [Fe—S] clusters, a protein scaffold to maintain those components and provide a stable reaction center and a source of electrons to drive the reduction reaction.

The present invention utilizes these elements of the molybdenum-containing domain 9 to bind nitrate 30 found in unknown test specimens. The active site, however, does not need to be chemically reduced to sense nitrate 30. Nitrate 30 is already bound to the molybdenum-molybdopterin (Mo-MPT) center 10 when the it is in oxidized form and so does not need to be reduced to bind nitrate 30.

Figure 7:
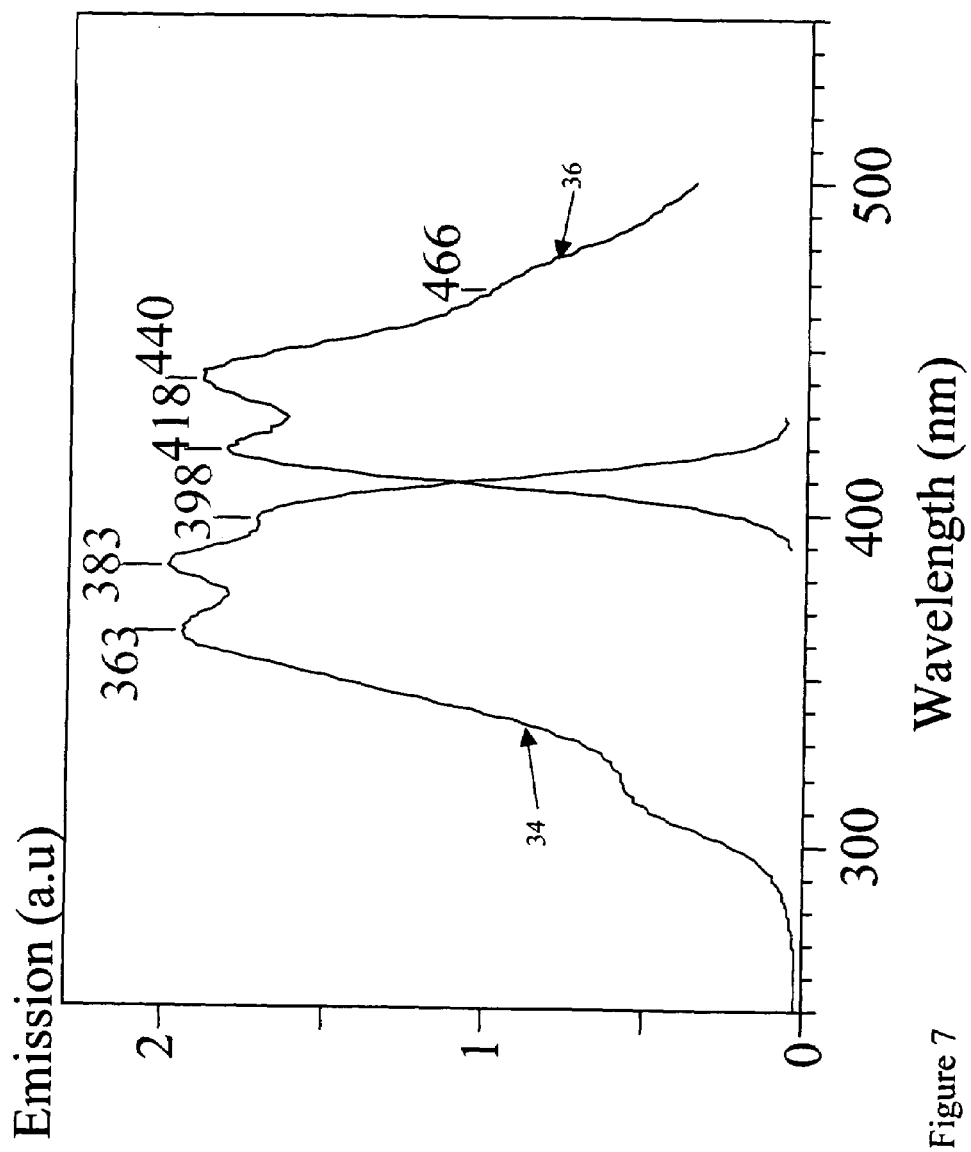
FIG. 7 is a graph of data showing the fluorescence excitation and emission profiles of Mo-MPT.
Figure 8:
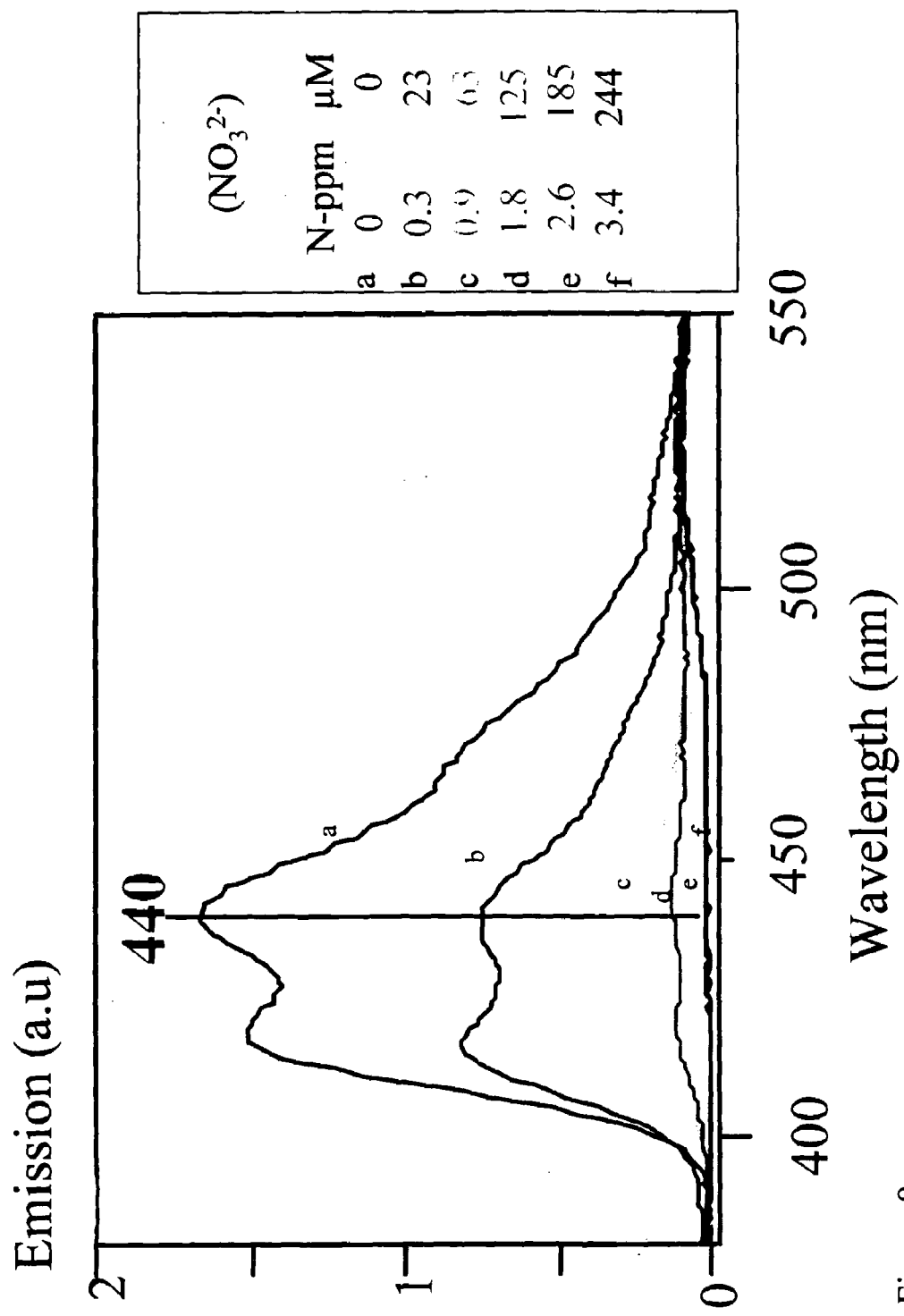
FIG. 8 is a graph of experimental results showing the fluorescence emission profiles of Mo-MPT quenched by various concentrations of nitrate.

Instead, the biosensor method of this invention uses fluorescence detection to sense nitrate 30 levels. Because Mo-MPT 10 naturally fluoresces as shown in FIG. 7, binding of nitrate 30 can be detected by monitoring the fluorescence signal associated with the Mo-MPT 10 to which it is bound. The Mo-MPT 10 fluorescence signal is quenched by the binding of nitrate 30. As a result, nitrate 30 can be detected and nitrate 30 levels can be determined by quenching of the fluorescence signal proportionally to the quantity of nitrate present. FIG. 8 shows a graph of the experimental results revealing the sensitivity of the method. The data shows detection of nitrate 30 levels as low as 0.3 parts per million (ppm) using this method.

Figure 14:
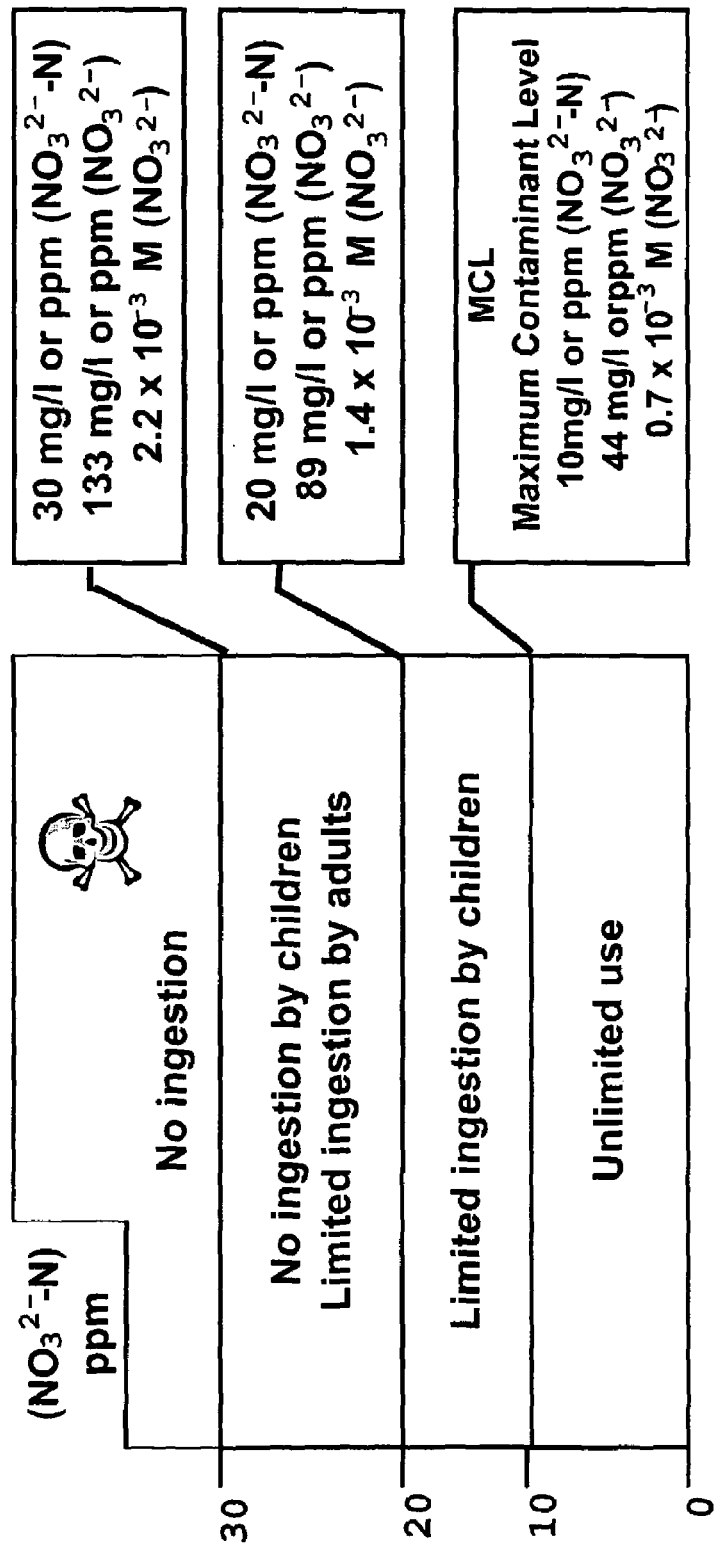
FIG. 14 is a table showing the sensitivity window for nitrate sensor applications.

Such a highly sensitive biosensor method or device has the advantage of being able to monitor minute amounts of nitrate 30 in applications such as those in the medical field which require detection of parts per million (ppm) concentrations of nitrate in urine and serum for diagnostic purposes as described in FIG. 14 (Table 1).

Figure 5:
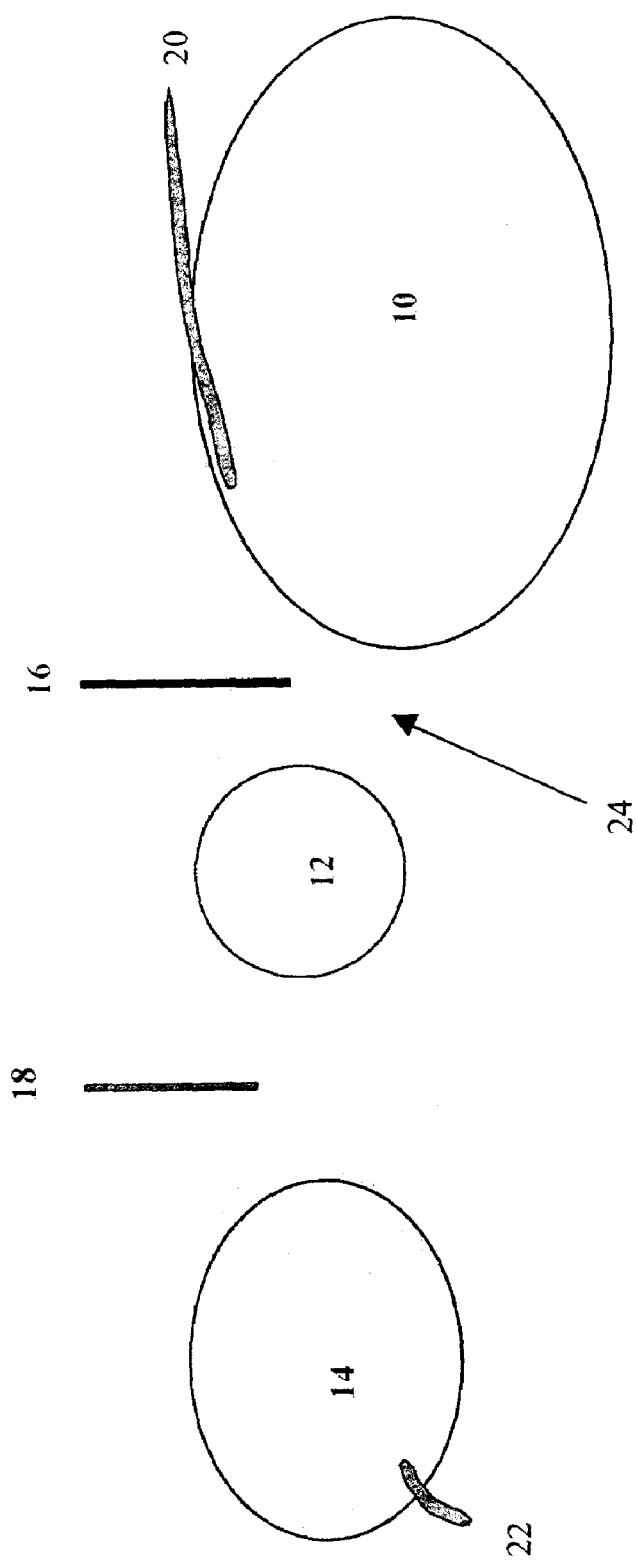
FIG. 5 is a schematic sequence model of nitrate reductase highlighting its three domains.
Figure 6:
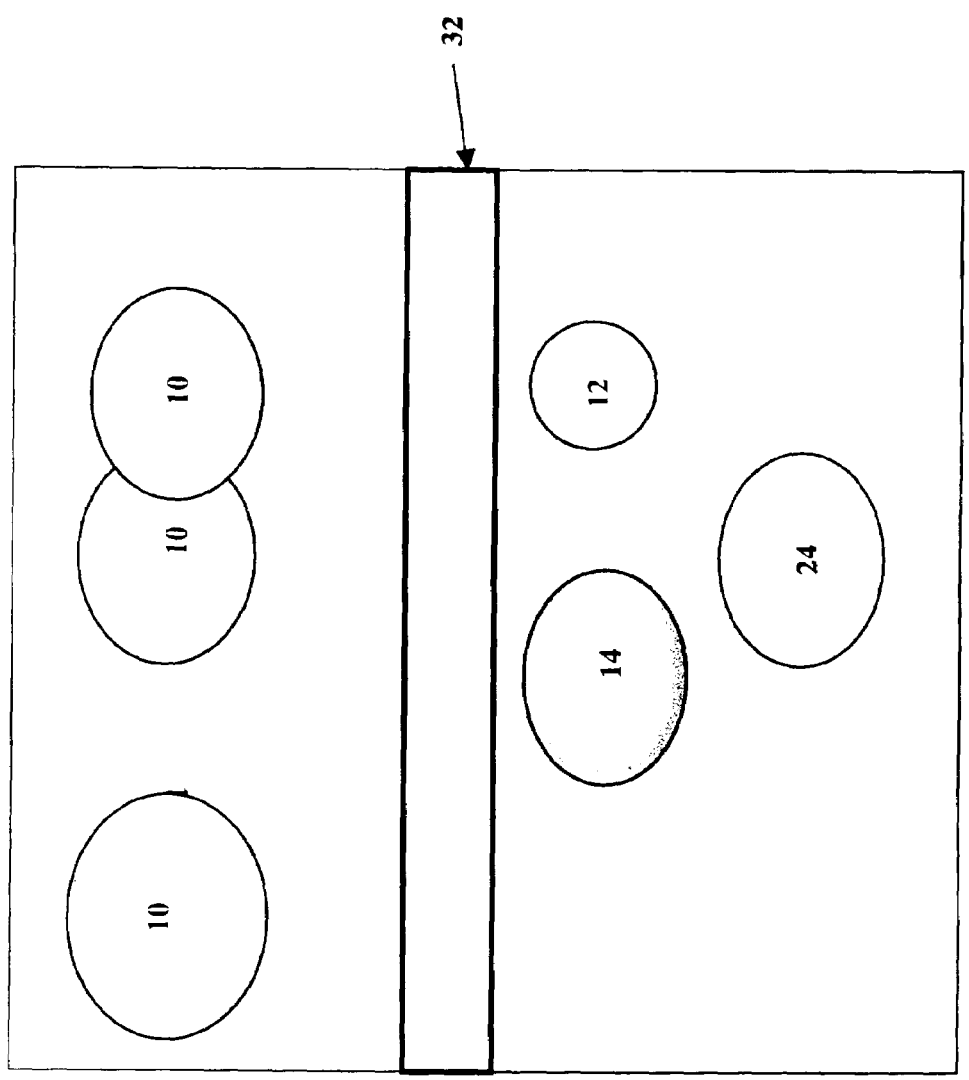
FIG. 6 is a schematic diagram representing filtration of the cleavage products of nitrate reductase.

In preferred embodiments of the invention, the Mo-MPT 10 is isolated from the nitrate reductase protein to remove confounding fluorescence signals potentially caused by the heme 12 and FAD 14 domains. If a Mo-MPT subunit is not readily available, it can be obtained by proteolytically cleaving the Mo-MPT 10 from a nitrate reductase polypeptide chain. Cleavage enzymes 24 commonly known in the art such as trypsin can be used to cleave between Mo-MPT 10 and Heme 12 at "hinge 1" 16 as shown in FIG. 5. The resulting Mo-MPT is approximately 56 kiloDalton (kDa) and may also result in 112 kDa dimers Mo-MPT, while the FAD 14 and Heme 12 domains connected by "hinge 2" are approximately 42 kDa and trypsin is approximately 24 kDa. Thus, the Mo-MPT can then be obtained by filtering the resulting cleavage products using a 50 kiloDalton (kD) cutoff filter 32 as depicted in FIG. 6.

Figure 11:
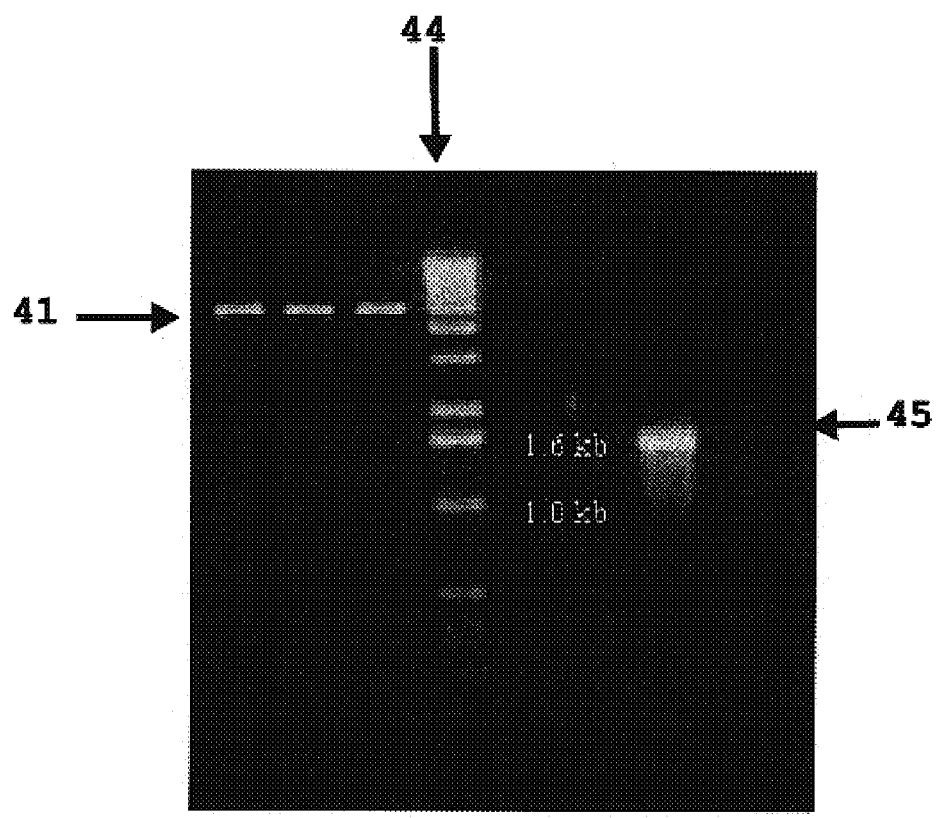
FIG. 11 is a picture of an electorphoresis gel confirming the PCR amplification of Mo-MPT gene fragment.

In another preferred embodiment, Mo-MPT 10 can be obtained by amplification and sub-cloning of the Mo-MPT 10 gene fragment. This employs, standard techniques, materials, and equipment used in gene cloning. (Sambrook, J., Frisch, E. F. and Maniatis, T. (1989) *Molecular Cloning: A Laboratory Manual, 2nd Edn.* Cold Spring Harbor Laboratory Press, Cold Spring Harbor, N.Y.) Based on this embodiment, FIG. 11 shows a 7% electrophoresis gel containing a Mo-MPT gene fragment 45 which was first amplified using polymerase chain reaction (PCR). The sample was then run on the electrophoresis gel shown in FIG. 11 which, in addition to showing the amplified Mo-MPT gene 45, also shows three blank controls 41 and a molecular weight marker 44.

Figure 12:
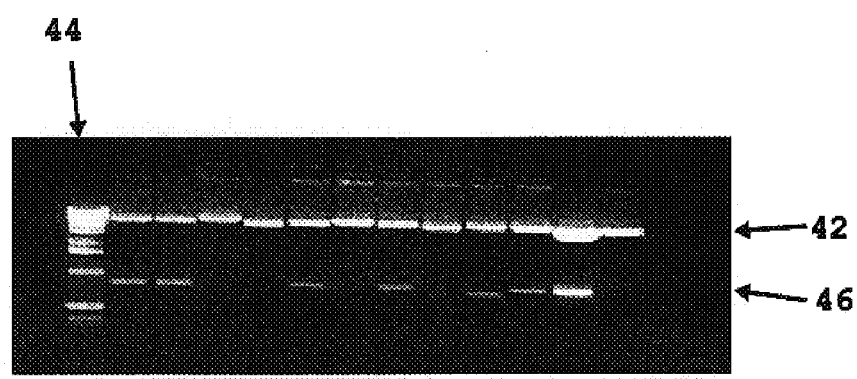
FIG. 12 is a picture of an electorphoresis gel confirming the positive insertion of sub-cloned Mo-MPT gene fragments into several vectors.

In another preferred embodiment of this method, large scale production of the Mo-MPT gene fragment 46 can be achieved by subcloning it using cloning vectors such as plasmids for protein expression and purification for production or manufacturing purposes. FIG. 12 represents a 7% agarose gel containing Mo-MPT gene fragments 46. The fragments were subcloned by insertion into a bacterial expression vector 42 and appear on the gel, thus indicating positive insertion of the fragments 46.

Once the Mo-MPT 10 is obtained, its initial fluorescence signal is measured. The excitation 34 and emission 36 spectra of Mo-MPT are shown in FIG. 7. As seen in the figure, the excitation occurs at about 370 nanometers (nm) and the emission occurs at about 450 nm. This fluoresence signal is proportionately quenched upon exposure to a nitrate-containing test specimen. FIG. 8 is a graph of quenching data obtained by adding various concentrations of nitrate ranging from 0.3 ppm to 3.4 ppm (samples a through f) to the Mo-MPT 10. As can be seen from the graphs, quenching of the emission signal is observed even by concentrations as low as 0.3 ppm or 23 micromoles of nitrate 30. Because quenching of the signal by nitrate 30 is concentration dependent, nitrate concentrations can be calculated based on the generation of a standard calibration curve of quenching values.

The quenched fluorescence (Q) is a function of the maximum possible quenching at an infinite nitrate concentration (Qmax) and the affinity of nitrate for its binding site (Kd) in the vicinity of its binding site, or Mo-MPT 10. Thus, it follows $$Q=(Q \max [\text{nitrate}])/(Kd+[\text{nitrate}])$$

where:
Q is the quenched fluorescence;
Qmax is maximal quenching at infinite concentration of nitrate; and
Kd is nitrate affinity for the binding site.

Quenching can also be considered in terms of:

$$F=Fo-Q$$

where:
F is the fluorescence in the presence of nitrate;
Fo is the fluorescence in the absence of nitrate; and
Q is the quenched fluorescence.

Figure 9:
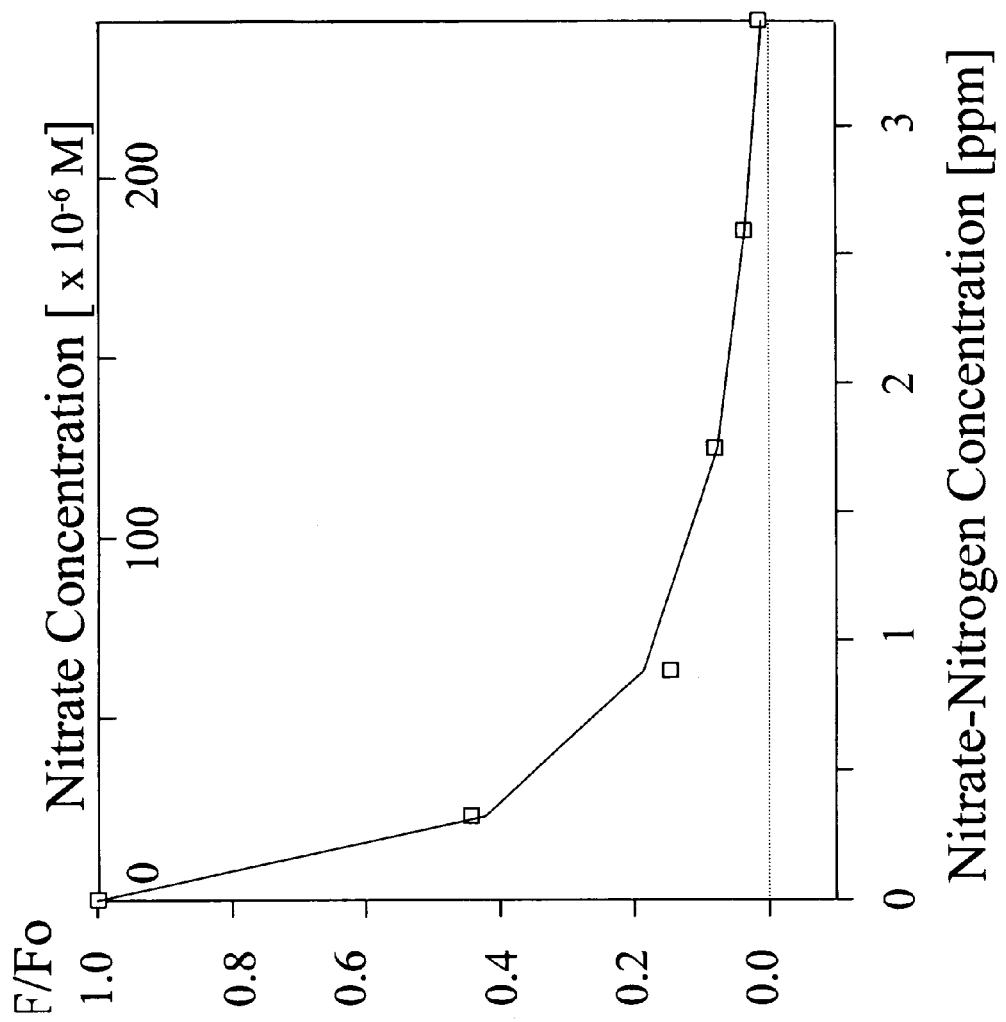
FIG. 9 is a graph of experimental results showing the fluorescence of Mo-MPT at 440 nanometes (nm) quenched by nitrate.

An example of data obtained by quenching Mo-MPT fluorescence at 440 nm by nitrate is shown in the graph of FIG. 9. The data was used to calculate Qmax and Kd based on the above equations. The resulting Qmax value is 1.07 and the corresponding Kd value is $20 \times 10^{-6}$ M. While the Qmax value exceeds unity, this is believed to arise through experimental artifacts. From these results it can be appreciated that nitrate 30 has a quenching effect on the fluorescence of Mo-MPT 10. Furthermore, the Kd value of $20 \times 10^{-6}$ M (representing nitrate 30 affinity for Mo-MPT 10) corresponds relatively well with the Michaelis constant ($K_m$) $13 \times 10^{-6}$ M of nitrate reduction, wherein the $K_m$ corresponds to the nitrate concentration at which the reaction is half maximal.

To further investigate the quenching of Mo-MPT 10 by nitrate 30, a comparison study was performed comparing quenching of Mo-MPT 10 versus FAD 14 by nitrate 30. The graph in FIG. 10 displays the results of the comparison. The data line labeled 38 represents quenching of FAD 14, while the data line labeled 40 represents quenching of Mo-MPT 10. As can be seen from these results, data line 38 is relatively flat over a concentration range of 0 to 20 ppm nitrate, thus representing dynamic quenching. This indicates that there is no specific interaction between the nitrate 30 and FAD 14. As a result, this type of quenching is simply controlled by the diffusion of nitrate. In contrast, data line 40 has a sharp and continuous decline in fluorescence over a concentration range of 0 to 4 ppm nitrate. This indicates that nitrate 10 is bound to the Mo-MPT 10 resulting in static quenching. Thus, the quenching is controlled by the affinity of nitrate 30 for Mo-MPT 10; and not simply by diffusion.

Figure 10:
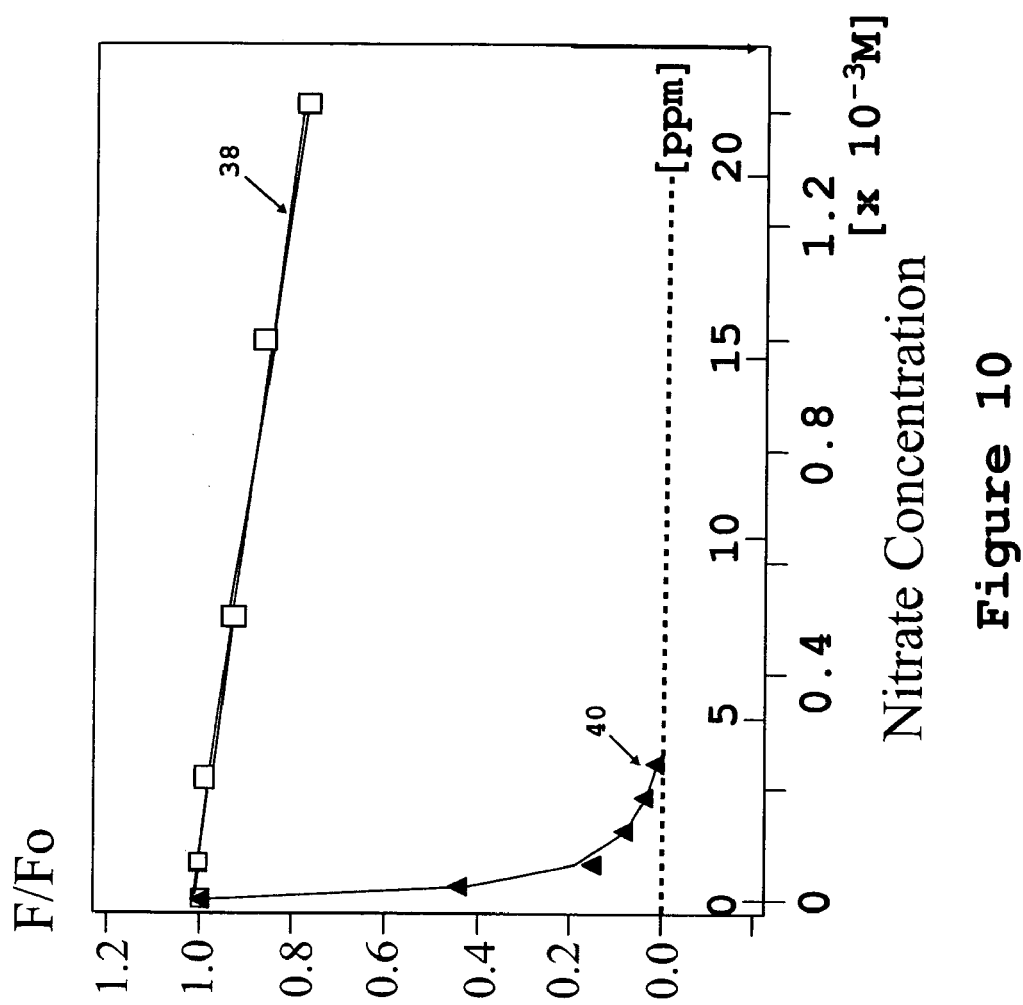
FIG. 10 is a graph of experimental results comparing fluorescence quenching of Mo-MPT and FAD by nitrate.

As can be seen from the experimental results in FIGS. 8 through 10, the biosensor method of the invention is highly sensitive. The data in these figures shows that the method is sensitive in ranges even as low as one part per billion. This level of high sensitivity allows the method to be relevant to measuring internal nitrate levels in living organisms. This opens the door to a wide range of applications in the medical, pharmaceutical and diagnostic fields.

Figure 13:
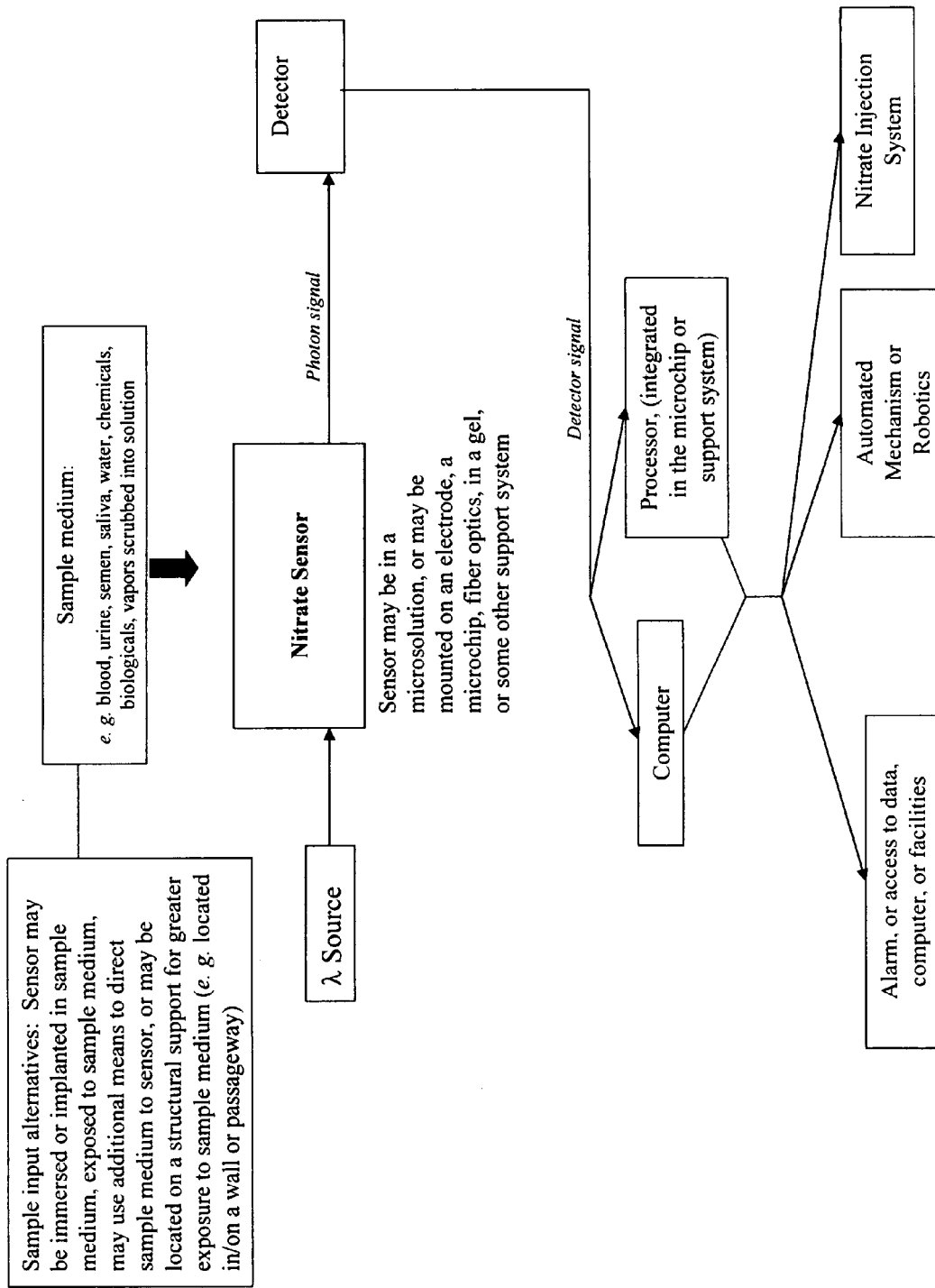
FIG. 13 is a block diagram showing the sensor applications and embodiments.

Furthermore, the small size of the biosensing elements; specifically the Mo-MPT 10, allow exposure to a test specimen in many ways as described in the diagram of FIG. 13. In particularly preferred embodiments, this includes immersing it in a solution microenvironment or implanting it into an organ e. g. circulatory system, or within a closed sample system.

Figure 3:
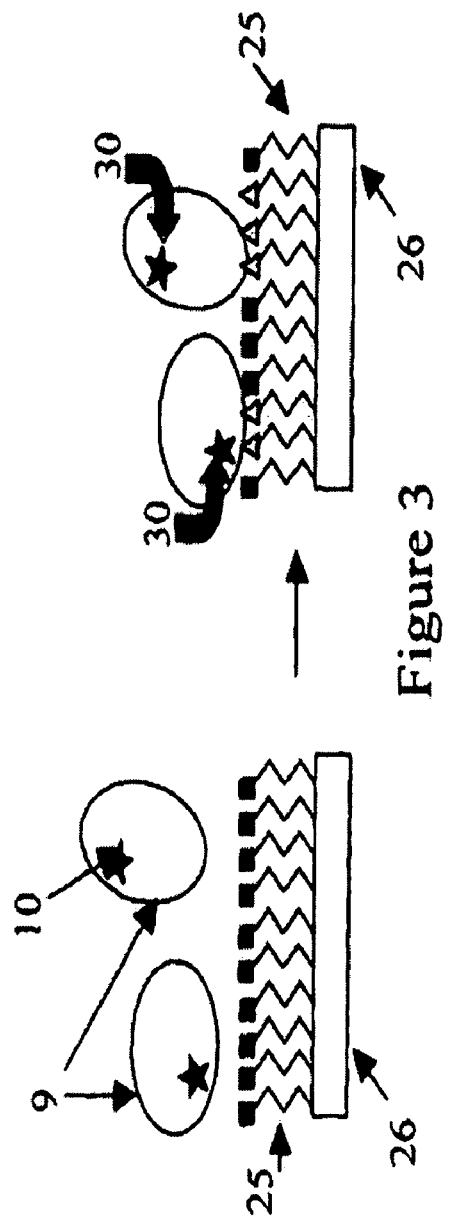
FIG. 3 is a schematic showing binding of nitrate and Mo-MPT to a substrate.

Additional preferred embodiments are shown in FIG. 3. This figure shows a molybdenum-containing domain 9 with the Mo-MPT 10 marked. After addition of nitrate 30, the nitrate-bound Mo-MPT unit is able to bind to open sites connecting via bridges 25 to a substrate 26. These bridges 25 may be examples of receptors extending from a self-assembling membrane as the substrate 26. The basic representation in this figure is that the nitrate biosensor method of the invention may be used as part of more complex series of receptor interactions for detection.

Figure 4:
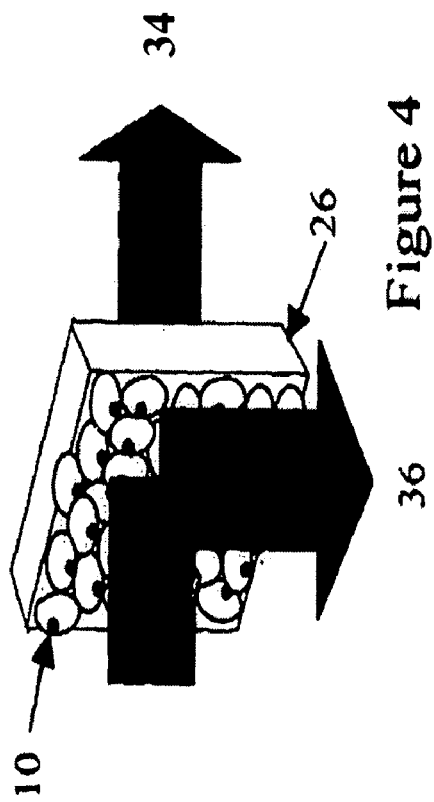
FIG. 4 is a schematic showing Mo-MPT disposed on a substrate as it is excited and emits fluorescence signals.

Yet another preferred embodiment is depicted in FIG. 4 which shows many of the Mo-MPT 10 units disposed on a substrate 26 for continuous reading of excitation 34 and emission 36. This embodiment of the method shows how multiple Mo-MPT 10 units can be arranged for specific detection needs.

Biosensor Apparatus

The preferred biosensor method and apparatus design yields the following benefits: 1) ultra-sensitivity as low as one part per billion; 2) the method can be performed on a large scale and the device can be mass produced; and 3) both the method and device are based on commonly used and readily available instrumentation.

A preferred embodiment of the invention includes a biosensor apparatus for detecting nitrate in test specimens. This implementation provides an embodiment of the present invention as part of a sensing system or apparatus. The apparatus includes an enclosure containing a fluorescence emitter such as the described Mo-MPT 10. It also includes means for adding a test specimen to the enclosure and a detector for sensing the fluorescence of the emitter and means for measuring any decrease in the sensed fluorescence after addition of test specimen.

A block diagram representing particularly preferred embodiments of the sensing system according to the invention is illustrated in FIG. 13. The diagram in FIG. 13 shows the nitrate sensor component of the sensing system as it is connected to a light source and a detector for receiving photon signaling.

In preferred embodiments, the nitrate sensor component may be in a microsolution, or may be mounted on an electrode, microchip, fiber optics, a gel, or some other structural support system. In other preferred embodiments noted in the diagram, the sensor may be immersed or implanted in a sample medium. Also, additional means to direct a test sample medium to the sensor may be added. Other such preferred embodiments include location of the sensor apparatus on a structural support for greater exposure to a test specimen or sample medium such as location in or on a wall, chamber, or passageway.

Once the sensor signal has reached the detector, the detector signal can be transmitted to a computer or processor for further automation as shown in FIG. 13. In particularly preferred embodiments of the invention, results can be monitored by an automated response such as an alarm or restricting access to data, computers or facilities. The automated response could also be used to control automated mechanisms or robotics as well as an automatic nitrate injection system. The electronic configurations and connections of these device are commonly known in the art and are further described in the references incorporated herein.

Modes of Use and Utility of the Invention

From the specific examples and the description herein of the invention, it is understood that the device can be modified for different sampling situations or regimes. The device is suitable for detection and quantification of nitrate levels relevant to public health, industrial and commercial processes including warfare agents and to environmental protection.

The device provides simple and flexible formats that allow for continuous flow-through assessments and for on-demand, single-sample or flow-through applications. The devices and methods of the invention are useful in a range of fields and applications. These include monitoring nitrate, in municipal drinking water facilities; in wastewater treatment facilities; for environmental assessments of natural fresh, marine and estuarine waters; and for medical diagnostics. The devices of the invention find use for process-control needs in industrial, pharmaceutical, nutritional-supplements, beverage, and foodstuff manufacturing industries; food process streams; assessment and process control of industrial process streams; in fermentation processes; and in human and veterinary medical diagnosis. The applications of the methods of using the device to detect biochemical levels in solution all involve the steps of causing the sensing elements of the device to be exposed to an analyte, and monitoring the response of the sensing elements.

Nitrate Monitoring and Quantification.

In a preferred embodiment, the device and methods of the invention find use in the monitoring and assessment of nitrate levels in a range of waters, many or most of which are required by federal and state agencies to protect human health and the environment. These include drinking water (ground waters, surface waters, processed waters); wastewater streams (septic systems, municipal and industrial waste water treatment); source waters for production of food stuffs, including processed foods and beverages; and industrial process streams, such as saltwater boilers, metal ore processing and mining activities for example.

In addition, the device and methods of the invention find use in environmental monitoring of freshwater sources (such as lakes and rivers), marine and estuarine waters (such as bays, harbors), coastal and open-ocean waters where nitrate levels are ever-increasing sources of anthropogenic pollution.

Nitrate levels in drinking water and foods and beverages are regulated because of the risks they pose to human health, and particularly to pregnant women and infants as shown in FIG. 14. In infants, the consumption of water or foods with levels of nitrate equal to or exceeding 10 mg/L or 1 mg/L nitrite can result in "blue-baby syndrome." This syndrome, which also can affect unborn fetuses, arises from an impaired oxygen-carrying capacity of hemoglobin in the blood due to the interaction of nitrite with hemoglobin. All consumed nitrate is rapidly reduced to nitrite by the bacterial flora of the stomach, making nitrite the toxic species. High nitrate levels in drinking water have also been linked to dramatically increased risks of certain cancers, particularly non-Hodgkin's lymphoma.

Accordingly, the present invention is not limited to the specific embodiments illustrated herein. Those skilled in the art will recognize, or be able to ascertain that the embodiments identified herein and equivalents thereof require no more than routine experimentation, all of which are intended to be encompassed by claims.

What is claimed is:

1. A biosensor method for detecting nitrate in a test specimen; said method comprising the steps of:
    exposing a fluorescence emitter to the test specimen;
    wherein said emitter consists of the Molybdenum-Molybdopterin (Mo-MPT) domain of nitrate reductase; and
    measuring any decrease in fluorescence of the emitter arising from the exposing step.

2. The method of claim 1, further comprising the step of:
    calculating a quantity of nitrate in the test specimen from the measured decrease in fluorescence.

3. The method of claim 2, wherein:
    the nitrate quantity is proportional to the measured decrease.

4. The method of claim 2, wherein:
    the nitrate quenches the fluorescence.

5. The method of claim 1, wherein:
    the nitrate quenches the fluorescence.

6. The method of claim 1, wherein:
    said emitter is obtained by cleaving the Mo-MPT domain of said nitrate reductase and isolating said cleaved domain.

7. The method of claim 6, wherein:
    the step of isolating the Mo-MPT domain occurs before said exposing step.

8. A biosensor method for detecting nitrate in a test specimen comprising the steps of:
    exposing a fluorescence emitter to a test specimen;
    measuring any decrease in fluorescence of the emitter arising from the exposing step;
    wherein the fluorescence emitter consists of the isolated Molybdenum-Molybdopterin (Mo-MPT) domain of nitrate reductase; and
    wherein said Mo-MPT domain is obtained by cleaving the Mo-MPT domain of the nitrate reductase to obtain a mixture of the cleaved Mo-MPT domain and nitrate reductase lacking the Mo-MPT domain, and then filtering the mixture to isolate the Mo-MPT domain.

9. A biosensor method for detecting nitrate in a test specimen comprising the steps of:
    exposing a fluorescence emitter to a test specimen;
    measuring a decrease in fluorescence of the emitter arising from the exposing step;

wherein the fluorescence emitter consists of the isolated Molybdenum-Molybdopterin (Mo-MPT) domain of nitrate reductase; and wherein said Mo-MPT domain is obtained by subcloning the Mo-MPT gene domain.

10. The method of claim 9, wherein the gene subcloning comprises the steps of:

inserting a cloned Mo-MPt domain into bacterial expression vectors to produce clone-inserted vectors;

screening said clone-inserted vectors for the presence of the Mo-MPT domain clone;

identifying vectors screening positive for the Mo-MPT domain clone from the vectors screening positive for the Mo-MPT domain.

11. The method of claim 10, wherein the gene subcloning further comprises the steps of, before the inserting step:

cleaving the Mo-MPt domain of the nitrate reductase; and amplifying the Mo-MPT domain, wherein the amplifying comprises using a polymerase chain reaction and subcloning of the Mo-MPT domain.

12. The method of claim 1, wherein:

the measuring step has a nitrate detection sensitivity on the order of one hundred parts per million, or better.

13. The method of claim 1, wherein:

the measuring step has a nitrate detection sensitivity on the order of ten parts per million, or better.

14. The method of claim 1, wherein:

the measuring step has a nitrate detection sensitivity on the order of one part per billion, or better.

15. The method of claim 1, wherein the exposing step comprises:

immersing the emitter in the specimen.

16. The method of claim 1, further comprising the step of, before the exposing step:

disposing the emitter on a structural support.

17. The method of claim 16, wherein:

the structural support comprises a wall of a chamber, room, or passageway.

18. The method of claim 16, wherein the structural support is selected from the group consisting of a gel matrix, a microsolution, an electrode, a microchip, a fiber-optic cable, and a solid particle.

19. The method of claim 1, further comprising the step of:

substantially continuously monitoring the specimen.

20. The method of claim 19, wherein the test specimen is selected from the group consisting of natural fresh, marine and estuarine waters, municipal and rural drinking water sources, aqueous solutions associated with wastewater treatment facilities, aqueous solutions associated with industrial process streams, pharmaceuticals, nutritional supplements, foodstuffs, beverages, body fluids, chemicals, water specimens, biologicals, vapors, and derivatives thereof.

21. A biosensor method for detecting nitrate in a test specimen comprising the steps of:

obtaining a fluorescence emitter from nitrate reductase, said obtaining step comprising isolating the domain consisting of the Mo-MPT domain of nitrate reductase in order to remove confounding fluorescence signals potentially caused by heme or FAD domains;

exposing the obtained fluorescence emitter to said test specimen; and measuring any decrease in fluorescence of said fluorescence emitter arising from said exposing step.

* * * * *